(12) United States Patent
Kamba et al.

(10) Patent No.: US 10,266,875 B2
(45) Date of Patent: Apr. 23, 2019

(54) EXTRACTION METHOD, ANALYTICAL METHOD, EXTRACTION DEVICE, AND ANALYTICAL DEVICE

(71) Applicant: Murata Manufacturing Co., Ltd., Nagaokakyo-shi, Kyoto-fu (JP)

(72) Inventors: Seiji Kamba, Nagaokakyo (JP); Takashi Kondo, Nagaokakyo (JP); Makoto Hasegawa, Nagahama (JP)

(73) Assignee: MURATA MANUFACTURING CO., LTD., Nagaokakyo-Shi, Kyoto-Fu (JP)

(\*) Notice: Subject to any disclaimer, the term of this patent is extended or adjusted under 35 U.S.C. 154(b) by 158 days.

(21) Appl. No.: 15/363,247

(22) Filed: Nov. 29, 2016

(65) Prior Publication Data
US 2017/0191114 A1 Jul. 6, 2017

Related U.S. Application Data

(63) Continuation of application No. PCT/JP2016/060693, filed on Mar. 31, 2016.

(30) Foreign Application Priority Data

May 29, 2015 (JP) .................. 2015-109904

(51) Int. Cl.
| | | |
|---|---|---|
| *C12Q 1/68* | (2018.01) | |
| *C12Q 1/04* | (2006.01) | |
| *C12Q 1/24* | (2006.01) | |
| *G01N 1/10* | (2006.01) | |
| *C12Q 1/6806* | (2018.01) | |
| *G01N 1/22* | (2006.01) | |
| *G01N 1/40* | (2006.01) | |
| *C12M 1/00* | (2006.01) | |

(52) U.S. Cl.
CPC ............. *C12Q 1/6806* (2013.01); *C12Q 1/04* (2013.01); *C12Q 1/24* (2013.01); *G01N 1/10* (2013.01); *G01N 1/2205* (2013.01); *G01N 1/2247* (2013.01); *G01N 1/4055* (2013.01); *C12M 47/10* (2013.01); *G01N 2001/1006* (2013.01); *G01N 2001/227* (2013.01); *G01N 2001/4061* (2013.01)

(58) Field of Classification Search
CPC combination set(s) only.
See application file for complete search history.

(56) References Cited

U.S. PATENT DOCUMENTS

| | | | |
|---|---|---|---|
| 6,777,228 B2 | 8/2004 | Lejeune | |
| 6,818,762 B2 * | 11/2004 | Rundell | ............... C12Q 1/6813 435/6.12 |
| 7,988,935 B2 | 8/2011 | Yuan et al. | |
| 8,053,214 B2 | 11/2011 | Northrup | |
| 8,685,746 B2 * | 4/2014 | Halverson | ............... G01N 1/38 422/400 |
| 9,433,883 B2 | 9/2016 | Takenaka et al. | |
| 2004/0043443 A1 | 3/2004 | Lejeune | |
| 2006/0051252 A1 | 3/2006 | Yuan et al. | |
| 2006/0246501 A1 | 11/2006 | Northrup | |
| 2013/0319239 A1 | 12/2013 | Takenaka et al. | |
| 2016/0041075 A1 | 2/2016 | Kamba et al. | |

FOREIGN PATENT DOCUMENTS

| | | |
|---|---|---|
| JP | H05-23181 A1 | 2/1993 |
| JP | 2005-520169 A | 7/2005 |
| JP | 2008-512128 A | 4/2008 |
| JP | 2015-188323 A | 11/2015 |
| WO | WO 2012/114458 A1 | 8/2012 |
| WO | WO 2014/192917 A1 | 12/2014 |

OTHER PUBLICATIONS

Hoshino et al.; "DNA Extraction from Soil"; Journal of Environmental Biotechnology, vol. 5, No. 1, pp. 43-53, 2005.
International Search Report issued for PCT/JP2016/060693, dated Jun. 28, 2016.
Written Opinion of the International Searching Authority issued for PCT/JP2016/060693, dated Jun. 28, 2016.

\* cited by examiner

*Primary Examiner* — David C Thomas
(74) *Attorney, Agent, or Firm* — Arent Fox LLP (57) ABSTRACT

The present invention is a method for extracting nucleic acid. A biological sample existing in a fluid is trapped using metal mesh. The biological sample contains nucleic acid and a coating structure covering the nucleic acid. The metal mesh with the biological sample trapped thereon is immersed in a nucleic acid extractant. The nucleic acid extractant is a solvent for the nucleic acid but not for the coating structure.

11 Claims, 7 Drawing Sheets
Specification includes a Sequence Listing.

FIG. 8

SEQUENCE LISTING

<160> NUMBER OF SEQ ID NOS: 4

<210> SEQ ID NO 1
<211> LENGTH: 22
<212> TYPE: DNA
<213> ORGANISM: Artificial Sequence
<220> FEATURE:
<223> OTHER INFORMATION: Synthetic Construct

<400> SEQUENCE: 1
tggcttcgtt catttataga ca        22

<210> SEQ ID NO 2
<211> LENGTH: 24
<212> TYPE: DNA
<213> ORGANISM: Artificial Sequence
<220> FEATURE:
<223> OTHER INFORMATION: Synthetic Construct

<400> SEQUENCE: 2
ctaaattgct tttgaatcat ccca        24

<210> SEQ ID NO 3
<211> LENGTH: 26
<212> TYPE: DNA
<213> ORGANISM: Artificial Sequence
<220> FEATURE:
<223> OTHER INFORMATION: Synthetic Construct

<400> SEQUENCE: 3 tttaaagag tttgatcmtg gctcag        26

<210> SEQ ID NO 4
<211> LENGTH: 26
<212> TYPE: DNA
<213> ORGANISM: Artificial Sequence

```
<220> FEATURE:
<223> OTHER INFORMATION: Synthetic Construct

<400> SEQUENCE: 4
ttaatacggy taccttgtta cgactt                                    26
```

EXTRACTION METHOD, ANALYTICAL METHOD, EXTRACTION DEVICE, AND ANALYTICAL DEVICE

CROSS REFERENCE TO RELATED APPLICATIONS

The present application is a continuation of International application No. PCT/JP2016/060693, filed Mar. 31, 2016, which claims priority to Japanese Patent Application No. 2015-109904, filed May 29, 2015, the entire contents of each of which are incorporated herein by reference.

TECHNICAL FIELD

The present invention relates to an extraction method, an analytical method, an extraction device, and an analytical device. More specifically, the present invention relates to an extraction method for extracting nucleic acid from a gas or a substance in a liquid, an analytical method that uses this extraction method, an extraction device, and an analytical device that uses this extraction device.

BACKGROUND OF THE INVENTION

Direct analysis of microbial or other DNA in the environment for purposes such as environmental manipulation has been focused on in recent years. In particular, techniques for the analysis of soil microbial DNA have been researched in various ways (e.g., see Hoshino et al. "DNA Extraction from Soil" Journal of Environmental Biotechnology, Vol. 5, No. 1, pp. 43-53, 2005 (Non Patent Document 1)). However, extracting DNA from such soil microorganisms requires troublesome operations, such as centrifugation.

Researchers have also been exploring ways to detect organisms such as bacteria and viruses by trapping biological samples in a fluid such as air or a liquid that contain bacterial, viral, and other nucleic acids and analyzing the nucleic acids in the trapped biological samples (e.g., identifying and quantifying the nucleic acids) using biological techniques, such as gene analysis, for purposes such as the prevention of hospital infections, preparation for pandemics, and health improvement in developing countries. At present, however, there is no established specific method for trapping atmospheric biological samples that contain nucleic acids and analyzing the nucleic acids.

Traces of biological samples in fluid such as air, unlike those in soil, are difficult to collect in sufficient quantities using techniques such as centrifugation. This would require filtering some large amount of air in such a manner that the trapped biological samples are concentrated on the filter.

However, the use of a known and commonly employed membrane or gelatin filters, for example, causes various problems. For example, when a membrane filter is used, it is difficult to collect a biological sample entrapped inside the complicated pore structure of the membrane filter. When a gelatin filter is used, the gelatin is denatured when exposed to atmospheric water. Likewise, collecting very minor biological samples in a liquid faces the problem of the need for troublesome operations, such as centrifugation.

Under these circumstances, it is an object of the present invention to provide an extraction method and an extraction device with which the user can trap a biological sample in a fluid through filtration and efficiently extract nucleic acid alone from the trapped biological sample.

BRIEF DESCRIPTION OF THE INVENTION

The invention includes a method for extracting nucleic acid. In accordance with this method, a biological sample existing in a fluid is trapped using metal mesh. The biological sample contains nucleic acid and a coating structure covering the nucleic acid. The metal mesh with the biological sample trapped thereon is immersed in a nucleic acid extractant. The nucleic acid extractant is a solvent for the nucleic acid but not for the coating structure. Thereafter nucleic acid extractant is collected. The extracted nucleic acid can then be analyzed.

In a preferred embodiment, the metal mesh has an aperture size which is smaller than the average size of the biological sample and larger than the average size of the nucleic acid. The metal mesh is preferably insoluble in the nucleic acid extractant and the nucleic acid extractant contains phenol and more preferably both phenol and choloform.

In a preferred embodiment, materials other than the biological sample are removed from the fluid using a pre-filter before the biological sample is trapped on the metal mesh.

Another preferred embodiment extracts nucleic acid from first and second biological samples existing in a fluid, the first biological sample having a different average size than the second biological sample. To this end, the first and second biological samples are trapped using first and second metal meshes, respectively. The first biological sample contains a first nucleic acid and a first coating structure covering the first nucleic acid. The second biological sample contains a second nucleic acid and a second coating structure covering the second nucleic acid. The first and second metal meshes, with the respective biological samples trapped thereon, are immersed in a nucleic acid extractant which is a solvent for both the first and second nucleic acids but is not a solvent for the first or second coating structures. Thereafter the first and second nucleic acid are separately collected.

The first metal mesh preferably has an aperture size which is smaller than the average size of the first biological sample and larger than the average size of the first nucleic acid. The second metal mesh preferably has an aperture size smaller than the average size of the second biological sample and larger than the average size of the second nucleic acid.

The invention is further directed towards an extraction device including a trap having a channel for a fluid and a metal mesh in the channel of the trap for trapping a biological sample existing in the fluid. The biological sample contains nucleic acid and a coating structure covering the nucleic acid. The extraction device further includes a container that holds a nucleic acid extractant that is a solvent for the nucleic acid but is not a solvent for the coating structure such that the metal mesh, and with it the biological sample trapped on the metal mesh, can be immersed in the nucleic acid extractant. An analyzer can be provided for analyzing nucleic acid extracted by the extraction device.

The metal mesh preferably has an aperture size which is smaller than the average size of the biological sample and larger than the average size of the nucleic acid. The metal mesh is preferably insoluble in the nucleic acid extractant.

In the preferred embodiment, the extraction device the nucleic acid extractant contains phenol and more preferably contains both phenol and chloroform.

In a preferred embodiment, the extraction device further includes a pre-filter located upstream of the metal mesh in the channel in the trap for removing a material other than the biological sample from the fluid. The trap may be a syringe barrel and the extraction device may include a gasket which is slidable in the syringe barrel to form a liquid tight seal and a plunger connected to the gasket.

The invention further includes an extraction device which includes a trap having a channel for a fluid and first and second metal meshes located in the channel for trapping first and second biological samples existing in the fluid. The first biological sample contains a first nucleic acid and a first coating structure covering the first nucleic acid. The second biological sample contains a second nucleic acid and a second coating structure covering the second nucleic acid. A container holds a nucleic acid extractant that is a solvent for both the first and the second nucleic acid but is not a solvent for either the first or the second coating structures such that the first metal mesh, and with it the first biological sample trapped on the first metal mesh, and the second metal mesh, and with it the second biological sample trapped on the second metal mesh, can be immersed in the nucleic acid extractant.

The first metal mesh preferably has an aperture size smaller than the average size of the first biological sample and larger than the average size of the first nucleic acid and the second metal mesh has an aperture size smaller than the average size of the second biological sample and larger than the average size of the second nucleic acid.

The present invention provides an extraction method and an extraction device with which the user can trap a biological sample in a fluid through filtration and efficiently extract nucleic acid alone from the trapped biological sample.

DESCRIPTION OF EMBODIMENTS

The following describes some embodiments of the present invention. In the drawings, the same reference numerals refer to the same or corresponding parts. Each embodiment is illustrative. Naturally, structures described in different embodiments may be partially replaced or combined with each other.

[Embodiment 1]
(First Step)

In this step, "a biological sample" in a fluid (e.g., a biological sample dispersed as particles in a fluid such as a gas or liquid) is trapped using metal mesh.

The biological sample includes nucleic acid and a coating structure covering the nucleic acid. The biological sample can be of any type of sample that contains nucleic acid, such as DNA or RNA. Examples include microorganisms, nucleic acid-containing structures, and cells. Examples of microorganisms include bacteria and fungi (true fungi). Other examples of nucleic acid-containing structures include viruses. When the biological sample is a microorganism or cell, the coating structure covering the nucleic acid is typically the cell membrane or the nuclear membrane. When the biological sample is a virus, the coating structure covering the nucleic acid is typically the capsid or the envelope.

The biological sample may also be a complex of examples mentioned above, such as a microorganism, a nucleic acid-containing structure, or cells, and another material, such as an inorganic or organic matter. Examples of such complexes include viruses attached to any vapor, including vapor in exhaled air, or inorganic particles. Examples of inorganic particles include atmospheric PM2.5, SPM, PM10, sand grains, and stones. The present invention is applicable even when the biological sample is in a form in which it is attached to a non-biological substance (particle).

Figure 1:
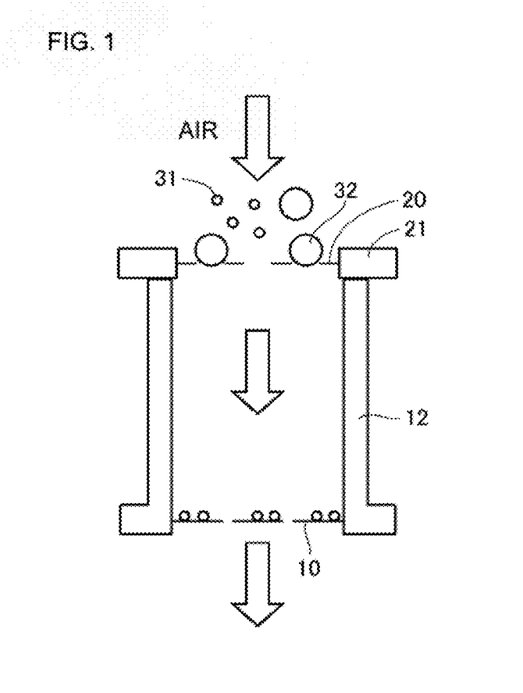
FIG. 1 is a cross-sectional schematic for illustrating an extraction method and an extraction device according to Embodiment 1.

Referring to FIG. 1, an extraction device used in this embodiment includes a syringe barrel (trap) 12 having a channel through which gas (e.g., air or an aerosol) can pass and a metal mesh 10 in the channel of the syringe barrel 12 for trapping a biological sample 31 as the gas passes through it. Passing gas through the channel of the syringe barrel 12 in the direction of the arrows in the drawing, using, for example, a suction device (not illustrated), causes the biological sample 31 in gas to be trapped on the metal mesh 10.

The metal mesh 10 preferably has an aperture size which is smaller than the biological sample. This leads to more reliable trapping of the biological sample on the metal mesh 10. The metal mesh 10 preferably has an aperture size larger than the nucleic acid. This prevents the nucleic acid from getting trapped on the metal mesh during the extraction of the nucleic acid from the biological sample trapped on the metal mesh 10.

The metal mesh is preferably insoluble in the nucleic acid extractant. This prevents the contamination of the nucleic acid extractant that would otherwise make the subsequent analysis less accurate. The details of the structure of the metal mesh 10 will be discussed below.

In this embodiment, there is a pre-filter 20 which is fastened by a fastener 21 to the inlet of the syringe barrel (trap) 12 upstream of the metal mesh 10 in the channel of the syringe barrel 12. This allows the user to remove impurities 32 from the biological sample 31. The pre-filter 20 has such an aperture size that the impurities 32 are blocked whereas the biological sample 31 is allowed to pass through.

This means that the first step preferably includes removing impurities, i.e, materials in the gas (aerosol) other than the biological sample, including complexes mentioned above using a pre-filter before trapping the biological sample on the metal mesh. This will make the analysis of the biological sample more accurate by limiting the amount of any impurity, or any material other than the biological sample which is trapped on the metal mesh.

Bacteria, for example, are on the order of 1 μm in size, and viruses are on the order of 0.1 μm in size. In many cases these bacteria and viruses, when suspended in air, are attached to other dispersed particles. Those particles can have a diameter of approximately between 0.1 μm and 100 μm. For this reason, the aperture size D1 of the pre-filter 20 and the aperture size of the metal mesh 10 are both, for example, between 50 nm and 500 μm with D1>D2. For example, when substantially spherical rotaviruses having a diameter of approximately 50 μm are attached to particles (sand grains) having a diameter of approximately 50 μm, D1 and D2 are, for example, selected to be 500 μm and 40 μm, respectively, with the aim of trapping the sand grains on the pre-filter 20 and trapping the rotavirus on the metal mesh 1.
(Second Step)

In this step, the metal mesh 10 with the biological sample 31 trapped thereon is immersed in a nucleic acid extractant.

Further details are described referring to FIGS. 2(*a*)-2(*d*). As illustrated in FIG. 2(*a*), a plunger 42 fitted to a gasket 41 is pushed to insert the gasket 41 into the syringe barrel 12. The gasket 41 forms a fluid tight seal with the inner edges of the syringe barrel 12. Then, as illustrated in FIG. 2(*b*), the tip of the syringe barrel 12 is dipped in a DNA extractant (nucleic acid extractant) 6 held in a container 5, and the plunger 42 is pulled upwardly and aspirate the DNA extractant 6 into the syringe barrel 12. This causes the metal mesh 10, with the biological sample 31 trapped thereon, to be immersed in the DNA extractant 6. Operations for DNA extraction, such as heating, are optionally performed in this state. This causes the DNA (nucleic acid) to be extracted from the biological sample 31 into the DNA extractant 6. The specific procedure for extraction can be any of various known techniques. A variety of known extractants for different nucleic acids are available as commercial products, such as kits, can be used.

The nucleic acid extractant is a solvent for the nucleic acid in the biological sample but not a solvent for the coating structure. This allows the user to selectively extract the nucleic acid from the biological sample using the nucleic acid extractant.

The nucleic acid extractant preferably contains an organic solvent (e.g., phenol or chloroform). This is advantageous in that the commonly used filters, such as membrane and gelatin filters, dissolve in organic solvents as a component of nucleic acid extractants, whereas the metal mesh in this embodiment does not dissolve in organic solvents.

It is preferred that the nucleic acid extractant contain phenol to ensure efficient DNA extraction. It is also preferred that the RNA extractant contain phenol because the phenol removes the coexisting DNA. The expression "the nucleic acid extractant contains phenol" means that the phenol is contained at least in the liquid in which the metal mesh having the biological sample trapped thereon is immersed. In an extractant kit, for example, not all liquids need to contain phenol.

It is also preferred that the nucleic acid extractant also contain chloroform. Although ensuring efficient DNA extraction, phenol is not completely isolated from the aqueous layer, i.e., part of it dissolves in the aqueous layer, in the liquid-liquid separation process. Phenol therefore makes the recovery process less efficient. Adding chloroform, a compound with a high degree of separation from the aqueous layer, brings the phenol to the organic layer side, thereby increasing the recovery of the DNA or other nucleic acid.
(Third Step)

Figure 2A:
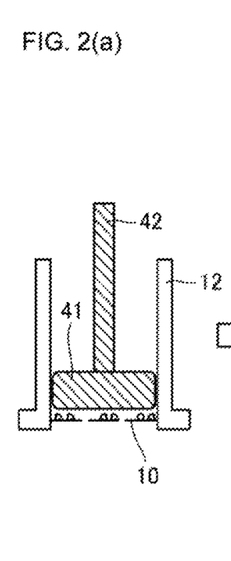
FIGS. 2(a)-2(d) are other cross-sectional schematics for illustrating an extraction method and an extraction device according to Embodiment 1.
Figure 2B:
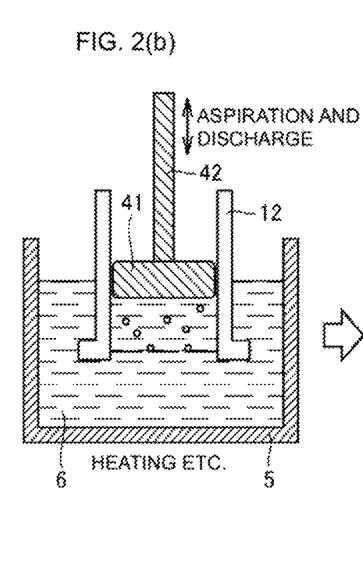
Figure 2C:
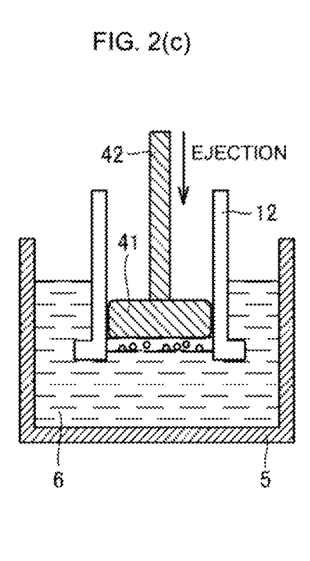
Figure 2D:
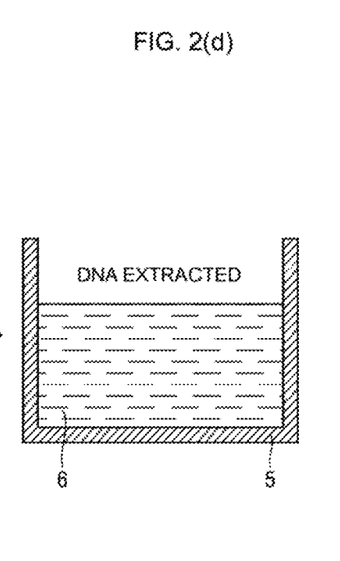

In this step, (at least part of) the nucleic acid extractant is collected to extract the nucleic acid. As illustrated in FIG. 2(*c*), after DNA (nucleic acid) has been extracted from the biological sample 31 into the DNA extractant 6, the plunger 42 is pushed down to slide the gasket 41 in the syringe barrel 12 and discharge the DNA extractant with the DNA therein into the container. The remainder of the biological sample 31 is trapped on the metal mesh 10 and therefore is separated from the DNA.

Then, as illustrated in FIG. 2(*d*), the syringe barrel 12 and the related components are removed together with the metal mesh 10 to leave the DNA extractant solution into which the DNA has been extracted. In this way, the user can extract nucleic acid from a biological sample existing in a gas.

The DNA (nucleic acid) extracted through this extraction method proceeds to, for example, polymerase chain reaction (PCR) amplification and then to analyses utilizing various known biological techniques, such as gene analysis (a fourth step).

When the biological sample is a microorganism, such as a bacterium, a treatment may precede the extraction of nucleic acid to culture and proliferate the trapped microorganism so that additional nucleic acid will be extracted.

In this embodiment, the microorganism is trapped on the metal mesh. It is therefore easy to transplant the microorganism to a medium by, for example, pressing the surface of the metal mesh with the microorganism trapped thereon against an agar or other medium to transfer the microorganism to the medium. If a commonly used membrane filter was utilized to trap the microorganism, it would be difficult to transfer the microorganism entrapped inside the pores of the filter to a medium, or to transplant the microorganism in a sufficient amount to a medium, by a similar method.

Figure 3:
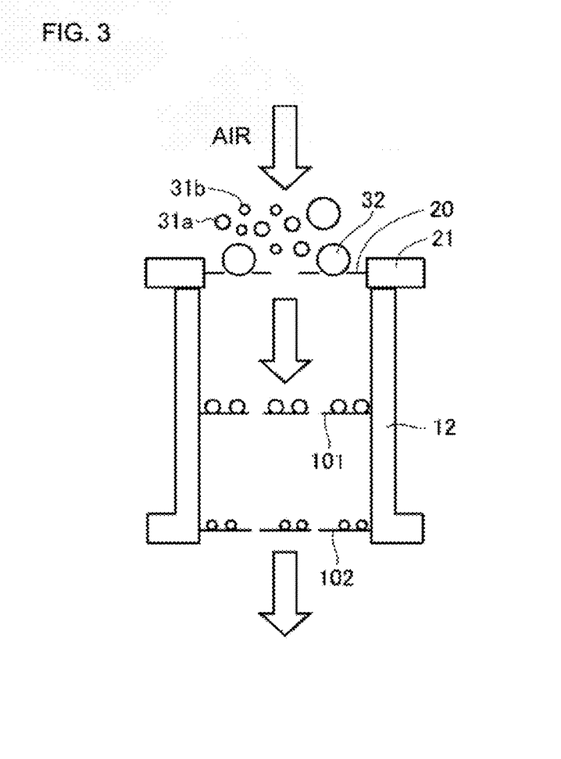
FIG. 3 is a cross-sectional schematic of a variation of Embodiment 1.

The following describes a variation of the foregoing embodiment. Referring to FIG. 3, the gas contains two biological samples 31*a* and 31*b* having different particle diameters. In this case, it is preferred that in the first step the biological samples 31*a* and 31*b* be separately trapped using multiple metal meshes 101 and 102 having different aperture sizes. In the second step, it is preferred that the metal meshes 101 and 102, with the respective biological samples 31*a* and 31*b* trapped thereon, be separately immersed in different nucleic acid extractants. The different biological samples are classified, and nucleic acids are extracted separately from the biological samples. This will make the analyses of the specific biological samples more accurate.

Figures 4A, 4B:
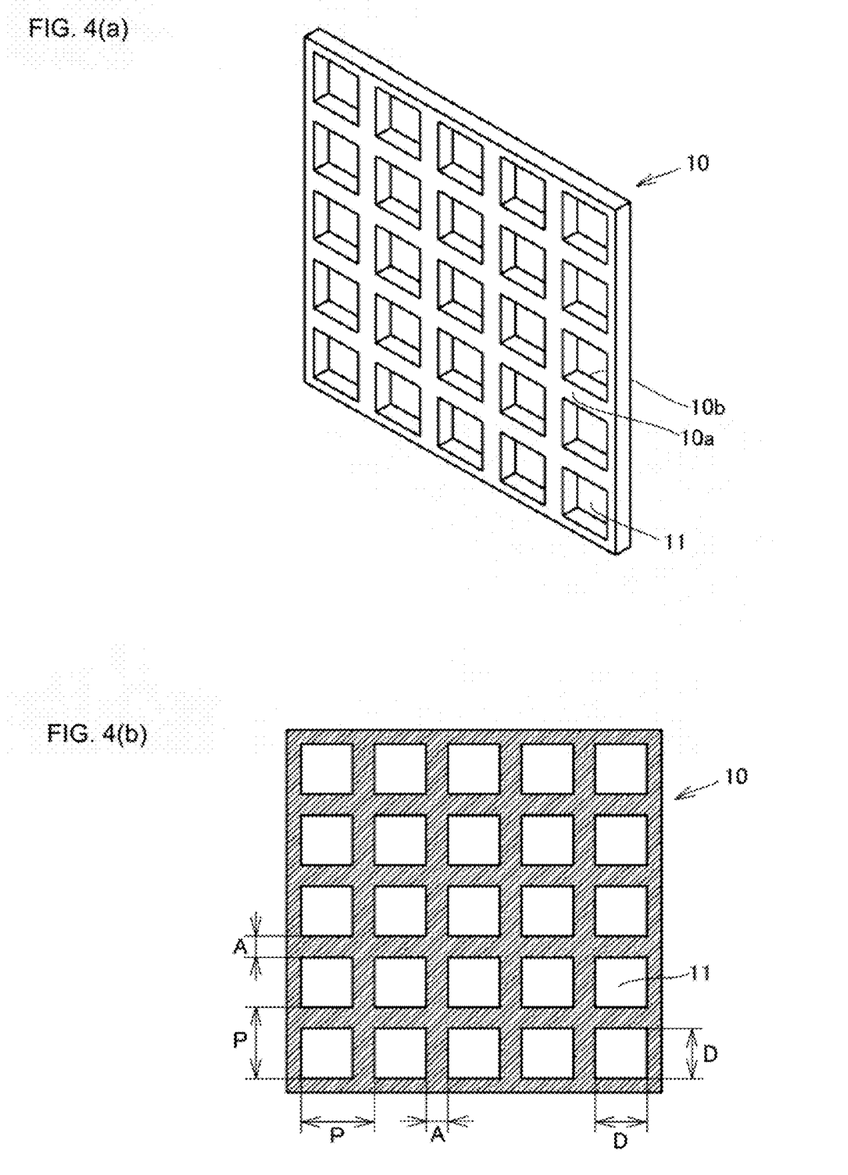
FIGS. 4(a) and 4(b) are a perspective and plan views, respectively, of the structure of an example of a metal mesh used in an embodiment of the present invention.

The following describes the structure of an example of metal mesh 10 used in an embodiment of the present invention with reference to FIG. 4. The metal mesh 10 in this embodiment is a sheet of metal mesh used to filter out a biological sample existing in a fluid (liquid or gas) and has multiple apertures 11 of such a size that the desired biological sample is blocked.

The metal mesh is preferably made of a metal or semiconductor. The metal can be of any kind, but examples include nickel, gold, silver, copper, iron, chromium, stainless steel, platinum, and titanium. Preferred examples are nickel, gold, silver, copper, platinum, titanium, and chromium, and more preferred examples are gold, platinum, and titanium.

The metal mesh 10 has a first principal surface 10*a* and a second principal surface 10*b* opposing the first principal surface 10*a*. The apertures 11 extend from the first principal surface 10*a* toward and through the second principal surface 10*b*. In other words, the apertures extend across the thickness of the metal mesh.

The metal mesh in this embodiment has, for example, multiple apertures 11 periodically arranged at least in one direction on the principal surfaces of the metal mesh. This provides a metal mesh with stable filtration characteristics.

By way of example, the apertures 11 are preferably arranged with regular spacing in a matrix (in a grid pattern) like that shown in FIG. 4(*b*). Specifically, it is preferred that the apertures 11 have a square shape when viewed from the first principal surface 10*a* side and are equally spaced in the two directions of arrangement parallel to the sides of the squares (the vertical and horizontal directions in the drawing). The arrangement of the apertures 11 may be such that some apertures are periodically positioned while others are not, unless this causes the filtration characteristics to become unstable.

The metal mesh may have a margin (not illustrated) around the apertures 11. The margin serves as, for example, a portion that a fastener holds to fasten the metal mesh during filtration.

The apertures 11 may have any size in which the biological sample can be trapped, but preferably, for example, a size that makes it physically impossible or difficult for the biological sample to pass through the mesh. Specifically, it is preferred that the metal mesh have an aperture size smaller than the biological sample.

The size of the apertures 11 (the aperture size of the metal mesh) is, for example, expressed as the diameter of circles inscribed in the apertures 11. For example, when the apertures 11 are square in shape as in FIG. 4(b), the diameter of the circles inscribing in the apertures 11 is the length D of the apertures 11.

The metal mesh has an aperture size smaller than the diameter of the biological sample. The diameter can be measured in various ways. For example, it can be the average diameter size of a predetermined number of particles of the biological sample. Alternatively, it can be the volume-average diameter (i.e., the diameter of the particles having an average volume). In this case, a graph showing the distribution of the volume and diameter of the samples being measured can be used and the diameter of the samples having an average volume will be the volume-average diameter. The measurement used is preferably the one that will ensure that the biological sample can be trapped using the metal mesh. Naturally, the aperture size of the metal mesh is such that the medium of the fluid (e.g., a gas or liquid) can pass through the mesh.

The metal mesh preferably has an aperture size larger than the nucleic acid. Again, the diameter of the nucleic acid can be measured as their number average diameter, their volume-average diameter or any other suitable measurement. The best choice of measures of size for the nucleic acid is based on whether the nucleic acid can pass through the metal mesh (whether the metal mesh traps the nucleic acid).

For example, when the metal mesh is one that has apertures 11 in a vertical and horizontal regular arrangement as in FIG. 4, it is preferred that the size of the apertures 11 (D in FIG. 4(b)) be, for example, equal to or smaller than the length of the longest point-to-point straight line extending through the biological sample on opposite surfaces of the biological sample.

The metal mesh 10 preferably has a frame width A (see FIG. 4(b)) of, for example, 0.5 μm or more and 100 μm or less.

The proportion of the open area provided by the apertures to the area of a principal surface of the metal mesh including the apertures 11 (hereinafter also referred to as the aperture ratio) is preferably 3% or more, more preferably 10% or more, for a faster flow of the fluid (gas) passing through the metal mesh. The aperture ratio is preferably 90% or less, more preferably 80% or less, for guarantee of the strength of the metal mesh. The aperture ratio can be adjusted by, for example, controlling the size of the apertures (primarily the apertures 11), which is indicated by D in FIG. 4(b), and the aperture pitch, indicated by P.

It is preferred to make the metal mesh as thin as possible but not so thin that it loses its required mechanical strength. This is because increasing the thickness of the metal mesh generally makes the pressure drop of the passing fluid larger. A large pressure drop through the metal mesh causes less efficient treatment and other problems as a result of a low flow rate and difficulty in passing the fluid. Specifically, it is preferred that the metal mesh have an average thickness of 0.2 μm or more and 40 μm or less, more preferably 0.5 μm or more and 5 μm or less.

The commonly used membrane and gelatin filters, which are relatively soft, are difficult to perforate with high precision for filtration pores. Even if high-precision pores were successfully created, it would be difficult to maintain the precision of the pores during storage and use. Worse yet, their low porosities have made the treatment time-consuming. Thus it has been impossible to trap the desired biological sample with selectivity and high precision in a short time, making it difficult to extract nucleic acid efficiently.

The metal mesh can be perforated with high precision for desired apertures, such as ones described above, at a high aperture ratio and maintains the precision of the apertures during storage and use. For this reason, a metal mesh is preferably used so that it is possible to trap the desired biological sample with selectivity and high precision and extract nucleic acid efficiently.

[Embodiment 2]

This embodiment is similar to Embodiment 1 but is different from Embodiment 1 in that the fluid is a liquid.

One of biological samples existing in liquids is Escherichia coli. There are various forms of E. coli, but they measure approximately 0.4 μm even along the shortest direction of axes. If one intends to, for example, trap E. coli in water, such as tap water or industrial water, the bacterium can be trapped with high efficiency when the diameter of the aperatures is equal to 200 nm.

[Embodiment 3]

This embodiment is different from Embodiment 1 in the second and third steps. The first step is the same as that of Embodiment 1.

The major operations in the second and third steps of this embodiment are (A) sample collection and cell disruption, (B) deproteinization, (C) DNA precipitation, and (D) DNA purification.

In this embodiment, the biological sample is trapped on metal mesh, and this provides more options for extracting nucleic acid in the second and third steps as compared with those that have hitherto been available with a membrane filter. Table 1 (below) summarizes various treatments of biological samples (bacteria, viruses, etc.) for disrupting (denaturing) any material other than nucleic acid, such as proteins (hydrophobic polymers), and extracting the nucleic acid, and compares the aptitude (resistance) of metal mesh and a membrane filter.

TABLE 1

| | | | Metal mesh (embodiment) | Membrane filter (comparative embodiment) |
|---|---|---|---|---|
| Biological sample treatments | Physical disruption | Heating | No limit (up to 1000° C.) | Up to 175° C. (autoclavable) |
| | | Bead beating Rapid freezing and grinding | Effective; the biological sample is exposed | Ineffective; the biological sample is adsorbed to the inside of pores |

TABLE 1-continued

|  |  | Metal mesh (embodiment) | Membrane filter (comparative embodiment) |
|---|---|---|---|
| Enzymatic disruption | Lysozyme Proteinase K Achromopeptidase Pronase | Easy to react; the biological sample is exposed | Difficult to treat; the biological sample is adsorbed to the inside of pores |
| Chemical disruption | Phenol and chloroform | Resistant | Not resistant |
|  | Benzyl chloride | Resistant | Prolonged use at a high concentration not allowed |
|  | Guanidine thiocyanate (GTC) | Resistant | Prolonged use at a high concentration not allowed |

As indicated in Table 1, the metal mesh-based embodiment offers a broader range of options than the membrane filter-based comparative embodiment for treatment conditions. The embodiment therefore allows for more efficient treatment (faster extraction) and extraction of more variations of cells.

For example, when a membrane filter, susceptible to phenol and chloroform, is used, it is impossible to extract nucleic acid directly from a biological sample trapped in the membrane filter using phenol and chloroform. Prior to the nucleic acid extraction, the biological sample needs to be separated from the membrane filter. Otherwise, dissolution of the filter can make the scanning of nucleic acid information in a subsequent step less sensitive. When metal mesh is used, it is possible to extract the nucleic acid using phenol and chloroform with the biological sample trapped on the metal mesh. This eliminates the need for prior separation of the biological sample from the membrane filter, thereby making the treatment more efficient.

The following describes specific examples of second and third steps of the embodiment as compared with the membrane filter-based comparative embodiment.

(1) Extraction of DNA from a Microorganism

Table 2 (below) provides an overview of the second and third steps for a case in which the nucleic acid is DNA and the biological sample is microorganism-containing dispersed particles. The treatments in Table 2, and those in Table 3 which will appear later herein, are listed in the order in which they are performed.

The membrane filter used in the comparative embodiment is, for example, a polyethersulfone membrane filter. This membrane filter is, for example, a commercial filter available as "Sterivex" (trade name: Merck Millipore, a pore size of 0.22 μm).

TABLE 2

| Embodiment (metal mesh) | Comparative embodiment (membrane filter) |
|---|---|
| SDS/Alkaline treatment | SDS (buffer) treatment |
| Phenol:chloroform extraction | Same as on the left |
| Chloroform extraction | Same as on the left |
| Ethanol precipitation | Same as on the left |

As indicated in Table 2, the embodiment is advantageous over the comparative embodiment in that the above SDS/alkaline treatment can be used. The comparative embodiment involves SDS (buffer) treatment, in which no alkali is used, because of the susceptibility of the membrane filter to alkalis.

SDS/Alkaline treatment is a treatment in which the metal mesh with the biological sample trapped thereon is immersed in an aqueous solution of surfactant SDS (sodium dodecyl sulfate) and alkali, and this treatment is intended to disrupt the proteins making up the microorganism by denaturing them before the extraction of DNA with solvents such as phenol. The treatment with an SDS solution (buffer) performed in the comparative embodiment is a similar process, but the SDS/alkaline treatment denatures the proteins faster by virtue of the presence of alkali.

Compared with the comparative embodiment, the embodiment shortens the overall duration of treatment and makes the treatment more efficient.

The addition of phenol or chloroform to an aqueous solution containing the metal mesh in the above phenol: chloroform extraction and chloroform extraction corresponds to the second step of the embodiment. The collection of the organic layer as a DNA solution in the phenol: chloroform extraction and chloroform extraction corresponds to the third step of the embodiment.

(2) Extraction of RNA from a Virus

Table 3 (below) provides an overview of the second and third steps for a case in which the nucleic acid is DNA and the biological sample is virus-containing dispersed particles.

TABLE 3

| Embodiment (metal mesh) | Comparative embodiment (membrane filter) |
|---|---|
| — | SDS (buffer) treatment |
| Treatment with a solution of phenol and guanidine thiocyanate | Same as on the left |
| Homogenization | Same as on the left |
| Addition of chloroform and collection of aqueous phase | Same as on the left |
| Isopropanol precipitation | Same as on the left |

As indicated in Table 3, the membrane filter-based comparative embodiment involves SDS (buffer) treatment, or immersing the membrane filter with the biological sample trapped therein in a buffer containing surfactant SDS, to extract the biological sample from the membrane filter into the buffer. Because of the susceptibility of the membrane filter to phenol and guanidine thiocyanate, this treatment needs to be conducted before the extraction of nucleic acid from the biological sample through treatment with a solution of phenol and guanidine thiocyanate. If the comparative embodiment excluded SDS (buffer) treatment and started with direct treatment with a solution of phenol and guanidine thiocyanate, it would be difficult to extract nucleic acid from the biological sample because issues such as occlusion of pores in the membrane filter would occur before the extraction of the nucleic acid.

In the metal mesh-based embodiment, the metal mesh with the biological sample trapped thereon is directly treated with phenol and guanidine thiocyanate. This separates the nucleic acid from the biological sample while separating the biological sample from the metal mesh. The embodiment therefore involves fewer treatment steps than the comparative embodiment. Compared with the comparative embodiment, this embodiment shortens the overall duration of treatment and makes the treatment more efficient.

The above treatment with a solution of phenol and guanidine thiocyanate and the addition of chloroform correspond to the second step of the embodiment. The collection of the aqueous layer following the addition of chloroform corresponds to the third step of the embodiment.

EXAMPLES

The following are specific examples using the present invention but the present invention is not limited to these examples.

Example 1

In this example, dust in air was trapped using an extraction device having a three-layer metal mesh, and the rotavirus in the trapped dust was extracted and detected.
(First Step: Trapping of Rotavirus)

Figure 5A:
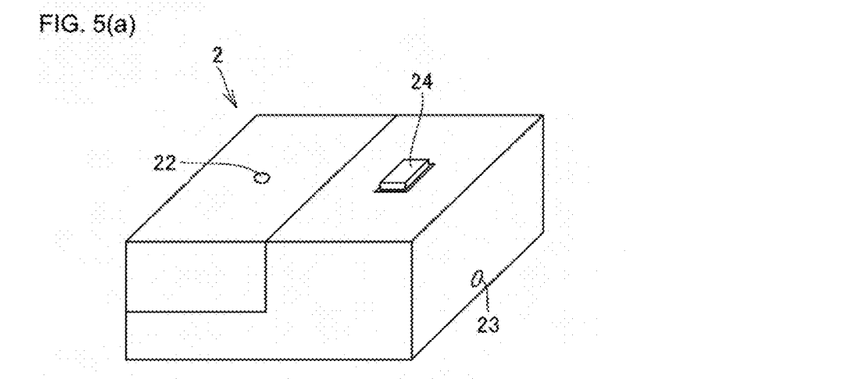
FIGS. 5(a)-5(d) are perspective, exploded perspective, cross-sectional and a partial enlarged views, respectively, of the structure of the extraction device used in Example 1.
Figure 5B:
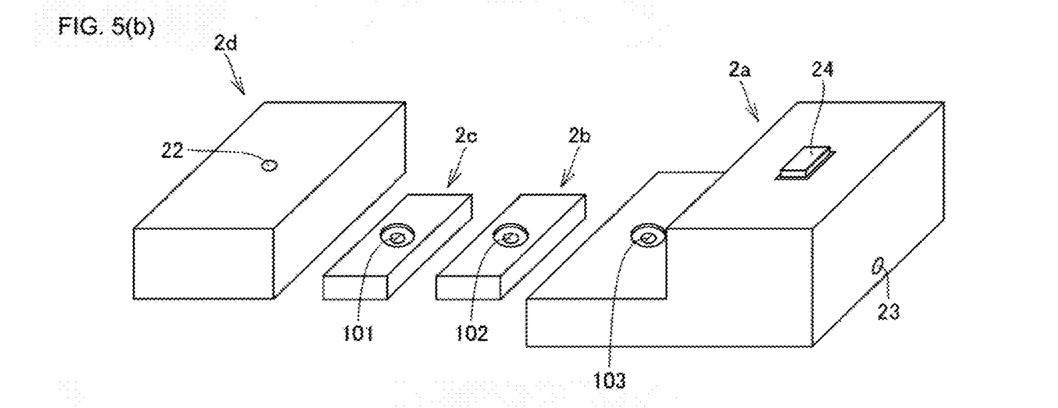
Figure 5C:
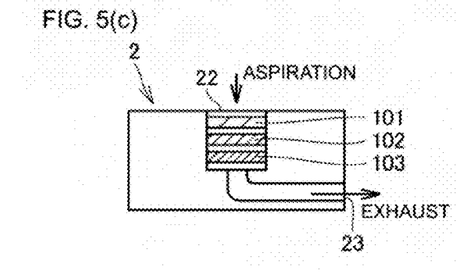
Figure 5D:
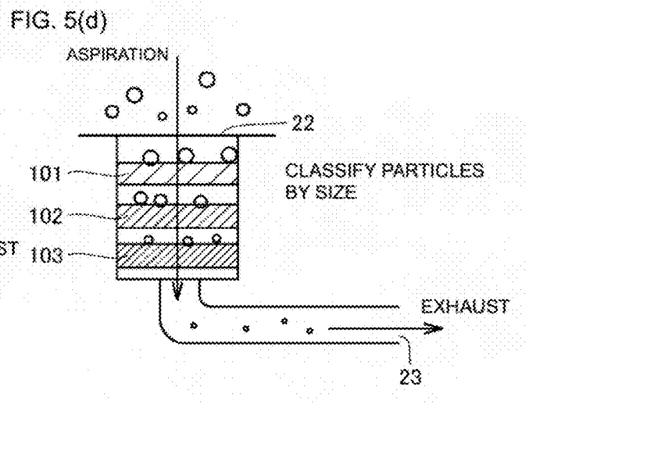
Figure 6:
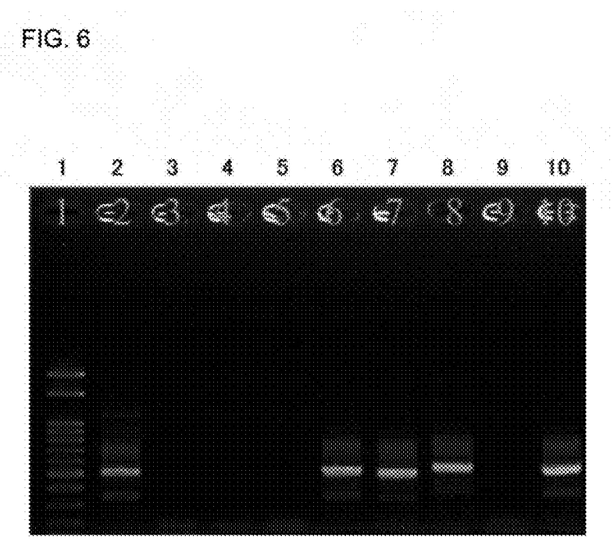
FIG. 6 is an electropherogram that represents the results of agarose gel electrophoresis from Example 1.

The lowermost mesh 103 is housed in a body 2*a* as shown in FIG. 5(*b*). An intermediate mesh 102 is housed in a stacking portion 102 and an upper mesh 101 is housed in a stacking portion 2*c*. The two stacking portions are housed (one stacked over the other) in a recess (not shown) formed in the bottom of cover 2*d*. Cover 2*d* (and with it stacking portions 2*b* and 2*c*) are placed on top of the lowermost mesh 103 so as to form the extraction device 2 best shown in FIG. 5(*a*). In this way, the three meshes 101, 102, and 103 are stacked on one another as best shown in FIG. 5(*c*). The fluid may then pass through meshes 101, 102 and 103 in that order. In this embodiment the aperature sizes of metal meshes 101, 102 and 103 are preferably 4.0 μm, 1.8 μm and 1.1 μm, respectively.

A cover 2*d* has an open space on its lower side in which the first stacking portion 2*b* and the second stacking portion 2*c* can be housed. Stacking the first stacking portion 2*b*, the second stacking portion 2*c*, and the cover 2*d* on the body 2*a* creates a channel that leads from an air inlet 22 to an air outlet 23 (FIG. 2(*c*)).

Referring to FIGS. 5(*c*) and 5(*d*), operating an aspiration switch 24 activates a pump contained in the body 2*a*. As a result, air is aspirated through the air inlet 22 and discharged through the air outlet 23. In this example, 55 liters of air was passed through between the air inlet 22 and the air outlet 23 over 2 hours to trap dust in the air on the metal mesh.

(Second and Third Steps: Collection of Nucleic Acid Extractant)

Then, nucleic acid (RNA) extractant was collected from the trapped dust.

First, the metal mesh 102 or the metal mesh 103 was put into a test tube with 0.75 mL of an RNA extraction reagent containing phenol and guanidine thiocyanate ("ISOGEN-LS," Code No. 311-02621, Nippon Gene). After standing at room temperature for 5 minutes, the test tube was stirred for 15 seconds with 0.2 mL of chloroform and allowed to stand at room temperature for 3 minutes. The metal mesh was then removed from the test tube.

The test tube was centrifuged using a high-speed centrifuge at 12000 g ("g" represents the acceleration of gravity) for 15 minutes to separate the contained water and organic solvent into two liquid phases. To the aqueous phase removed from the test tube, 0.5 mL of isopropanol was added to precipitate RNA. The residue after the removal of the liquid was similarly treated with 70% ethanol to wash the precipitate. The precipitate (containing RNA if the dust contained RNA) was dissolved in 50 μL of water and purified using a nucleic acid purification kit (One Step PCR Inhibitor Removal Kit: Zymo Research) to remove PCR inhibitors such as corrosion acid (humic acid). Lastly, the product was eluted in 50 μL of water, and the "RNA extract" was collected.

(Fourth Step: Analysis of the Nucleic Acid)

Additionally, the RNA in the "RNA extract" (RNA of viral origin) was converted into DNA through reverse transcription according to the following method.

Specifically, cDNA was prepared from the RNA (such as the VP4 gene of rotavirus) through a reverse transcriptase reaction using a reverse transcription kit ("ReverTra Ace® qPCR RT Kit," Code No. FSQ-101, Toyobo).

Many of the reagents mentioned below are included in this kit.

First, the following materials were mixed: 9 μL of water free of RNAase ("RNase-free Water," Takara Bio), 3 μL of DMSO (dimethylsulfoxide), 1 μL of primer (synthetic oligonucleotides that amplify the VP4 gene of rotavirus, with sequences of 5'-TGGCTTCGTTCATTTATAGACA-3' (SEQ ID NO: 1) and 5'-CTAAATTGCTTTTGAATCATCCCA-3' (SEQ ID NO: 2)) , and 2 μL of the aforementioned "RNA sample solution." The resulting liquid mixture was heated at 97° C. for 2 minutes and allowed to cool on ice for 2 minutes.

Fifteen microliters of the liquid mixture was mixed with 7.5 μL of "RNase-free Water," 6 μL of "5× RT buffer" (a five-fold concentrated reverse transcription buffer containing reaction buffer, MgCl2, dNTPs, etc.; Toyobo), and 1.5 μL of "Enzyme Mix" (an enzyme mixture of "ReverTra Ace®" and "RNase inhibitor," Toyobo). The resulting liquid mixture was heated and cooled under the following conditions to allow reverse transcription to proceed: 42° C. for 30 minutes, 97° C. for 5 minutes, and then 4° C. at 5 minutes.

Then PCR-based rotavirus gene detection was performed using an enzyme solution for PCR ("KOD-Plus-Ver. 2" Code No. KOD-211, Toyobo).

First, the following materials were mixed: 14 μL of "RNase-free Water," 2.5 μL of "10×Buffer for KOD-Plus-Ver. 2 " (Code No: KOD-3B, Toyobo), 2.5 μL of an aqueous solution of dNTPs (2 mM), 1.5 μL of an aqueous solution of MgSO4(25 mM), 1 μL of DMSO, 0.5 μL of "KOD-plus-Ver. 2," and 1 μL of primer (synthetic oligonucleotides that amplify the VP4 gene of rotavirus, with sequences of 5'-TGGCTTCGTTCATTTATAGACA-3' (SEQ ID NO: 1) and 5'-CTAAATTGCTTTTGAATCATCCCA-3' (SEQ ID NO: 2)).

The resulting liquid mixture was subjected to 35 cycles of PCR, with each cycle consisting of heating at 95° C. for 2 minutes first, then 94° C. for 30 seconds, 48° C. for 30 seconds, and 72° C. for 1 minute. The mixture was lastly heated at 72° C. for 7 minutes and cooled at 4° C. for 10 minutes to give a DNA sample solution. The DNA sample solution was analyzed by agarose gel electrophoresis, with results (an electropherogram) presented in FIG. 6.

In FIG. 6, lane 1 was for the migration of a molecular weight marker (100 bp DNA Ladder H3 RTU, GeneDireX). Lanes 3 and 4, lanes 5 and 6, lanes 7 and 8, and lanes 9 and 10 were for the migration of DNA sample solutions obtained from dust in air trapped at different locations. The odd-number lanes (lanes 3, 5, 7, and 9) were allotted to DNA sample solutions obtained from the metal mesh 102 (aperture size: 1.8 μm), whereas the even-number lanes (lanes 4, 6, 8, and 10) to those from the metal mesh 103 (aperture size:

1.1 µm). Lane 2 was used to run a positive control, a similar DNA sample solution obtained from cultured rotavirus.

In lanes 6 to 8 in FIG. 6, a band was observed at a position similar to that of the DNA obtained from rotavirus (lane 2). The DNA sample solutions run in lanes 6 to 8 therefore contained rotavirus-derived DNA, suggesting that the air at the locations corresponding to the samples in lanes 6 to 8 contained rotavirus.

Example 2

Dust in air was trapped in the same way as in Example 1. Then, respective test tubes containing the metal mesh 101, the metal mesh 102, and the metal mesh 103 therein were prepared. A 700 µL of SL1 buffer (an SDS solution) was contained in a nucleic acid extraction kit ("NucleoSpin® Soil," Code No. U0780A (distributed in Japan by: Takara Bio), Macherey-Nagel), and then a 150 µL of "Enhancer SX" solution, also contained in the kit, were added to the test tubes. The resulting liquid mixture was vigorously agitated at room temperature for 5 minutes.

After a 2-minute centrifugation at 11000 g, the mixture was stirred with 150 µL of SL3 buffer ("Lysis Buffer SL3," Takara Bio) and then allowed to stand at 4° C. for 5 minutes. The mixture was then centrifuged at 11000 g for 1 minute, and the supernatant (a sample) was collected. A mixture of the supernatant and SB buffer ("Binding Buffer SB," Takara Bio) was passed through an equilibrated mini-spin column ("NucleoSpin Inhibitor Removal Column," Takara Bio) to make the extracted DNA in the sample adsorbed.

The column was then washed with 500 µL of SB buffer, 550 µL of SW1 buffer ("Wash Buffer SW1," Takara Bio), and 700 µL of SW2 buffer ("Wash Buffer SW2," Takara Bio) by passing them through the column in this order. Then 30 µL of SE buffer ("Elution Buffer SE," Takara Bio) was passed to elute the DNA out of the column, giving a DNA extract.

The 16S rDNA sequence was then amplified using "Bacterial 16S rDNA Clone Library Construction Kit" (Takara Bio). First, the following materials were mixed: 5 µL of the DNA extract, 25 µL of "2×Gflex PCR buffer" (Takara Bio), 1 µL of primer cocktail [a liquid mixture of "16S-FA PCR primer" (5'-TTTTAAAGAGTTTGATC(A/C)TGGCTCAG-3' (SEQ ID NO: 3)) and "16S-R3PCR primer" (5'-TTAATACGG(C/T)TACCTTGTTACGACTT-3' (SEQ ID NO: 4))], 1 µL of "Tks Gflex DNA polymerase" (Takara Bio), and 18 µL of "DNA free water" (Takara Bio).

The resulting liquid mixture was subjected to 35 cycles of PCR, with each cycle consisting of heating at 94° C. for 1 minute first, then 98° C. for 10 seconds, 55° C. for 15 seconds, and 68° C. for 45 seconds. The mixture was lastly cooled at 4° C. for 10 minutes to give a DNA sample solution (a solution containing a PCR amplification product). The DNA sample solution was analyzed by agarose gel (1.2%) electrophoresis, with results (an electropherogram) presented in FIG. 7.

Figure 7:
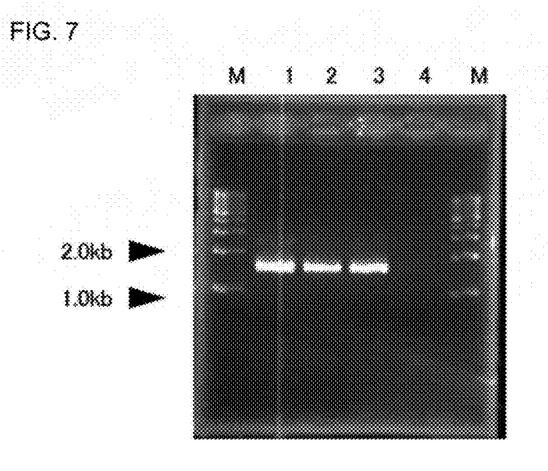
FIG. 7 is an electropherogram that represents the results of agarose gel electrophoresis from Example 2.

In FIG. 7, lane M was for the migration of 2 µL of a molecular weight marker ("1 kb DNA ladder," Takara Bio). In lane 1, 10 µL of the DNA sample solution obtained from the metal mesh 101 (aperture size: 4.0 µm) was run. In lane 2, 10 µL of the DNA sample solution obtained from the metal mesh 102 (aperture size: 1.8 µm) was run. In lane 3, 10 µL of the DNA sample solution obtained from the metal mesh 103 (aperture size: 1.1 µm) was run. Lane 4 was used to run 10 µL of negative control.

In lanes 1 to 3 in FIG. 7, a band was observed for a roughly 1.5-kb DNA. The DNA sample solutions obtained in this example therefore contained a roughly 1.5-kb PCR amplification product derived from 16 S rDNA, demonstrating that genes were successfully extracted in analyzable amounts from microorganisms in dust.

Example 3

In this example, the DNA sample solutions (PCR products) run in lane M and lanes 1 to 4 in Example 2 were each analyzed using a library construction kit for environmental bacterial community structure characterization ("Bacterial 16 S rDNA Clone Library Construction Kit" (Takara Bio)). In other words, DNA in the DNA sample solution was inserted into a plasmid vector, and *E. coli* plasmid clones were isolated. The DNA insert of 100 clones was sequenced. The details are as follows.

First, 1 µL of the DNA sample solution (16 S rDNA PCR product) was mixed with 1 µL of "pBackZero-alpha linear vector" plasmid vector-containing solution (50 ng/µL), 5 µL of "DNA Ligation Kit <Mighty Mix>," and 5 µL of "DNA free water," all supplied with the kit. Then the reaction was allowed to proceed at 16° C. for 30 minutes to insert the DNA into the plasmid vector. The resulting plasmid vector was introduced into *E. coli* ("*E. coli* HST08 Premium Competent Cell," Takara Bio).

Plasmids were extracted and purified from a monoclonal culture of the *E. coli* using "PureYield Plasmid Miniprep System" (Promega). These plasmids were sequenced according to the standard method using "ABI PRISM(R) 3100 Genetic Analyzer." The following tables list the microorganisms (bacteria) identified through a BLAST search for the sequences.

TABLE 4

| clone No. | taxonomy ID | blast name | Bacteria |
|---|---|---|---|
| 1 | | | Unsequenceable |
| 2 | 77133 | Uncultured bacterium | 98% homologous with GenBank: EU160322.1 *Bacillus* sp. |
| 3 | 904978 | high GC Gram+ | uncultured *Quadrisphaera* sp. |
| 4 | | | Unsequenceable |
| 5 | 764360 | g-proteobacteria | *Acinetobacter* sp. WJ07 |
| 6 | | | Plasmid low yield |
| 7 | 106649 | g-proteobacteria | *Acinetobacter guillouiae* |
| 8 | 77133 | Uncultured bacterium | 95% homologous with GenBank: GU117230.1 *Beijerinckia* sp. |
| 9 | | | Plasmid low yield |
| 10 | 764360 | g-proteobacteria | *Acinetobacter* sp. WJ07 |
| 11 | 764360 | g-proteobacteria | *Acinetobacter* sp. WJ07 |
| 12 | | | Unsequenceable |
| 13 | | | Plasmid low yield |
| 14 | | | Unsequenceable |
| 15 | 106649 | g-proteobacteria | *Acinetobacter guillouiae* |
| 16 | | | No insertion into vector |
| 17 | 165433 | g-proteobacteria | uncultured *Acinetobacter* sp. |
| 18 | 77133 | Uncultured bacterium | 99% homologous with GenBank: JQ386426.2 Acetobacteraceae bacterium |
| 19 | | | Unsequenceable |
| 20 | 550 | enterobacteria | *Enterobacter cloacae* |
| 21 | 1747 | high GC Gram+ | *Propionibacterium acnes* |

TABLE 4-continued

| clone No. | taxonomy ID | blast name | Bacteria |
|---|---|---|---|
| 22 | | | Plasmid low yield |
| 23 | 77133 | Uncultured bacteria | 99% homologous with GenBank: JQ386372.2 Acetobacteraceae bacterium |
| 24 | 106649 | g-proteobacteria | *Acinetobacter guillouiae* |
| 25 | 77133 | Uncultured bacteria | 98% homologous with GenBank: JQ769678.1 *Leptolyngbya frigida* |
| 26 | | | Unsequenceable |
| 27 | 563057 | a-proteobacteria | proteobacteria |
| 28 | 93925 | liverworts | *Marchantia paleacea* subsp. *diptera* |
| 29 | 1747 | high GC Gram+ | *Propionibacterium acnes* |
| 30 | 106649 | g-proteobacteria | *Acinetobacter guillouiae* |
| 31 | 77133 | Uncultured bacteria | 99% homologous with GenBank: JQ386099.2 Acetobacteraceae bacterium |
| 32 | | | Unsequenceable |
| 33 | 77133 | Uncultured bacteria | 99% homologous with GenBank: JQ383553.2 *Roseomonas frigidaquae* |
| 34 | 93925 | liverworts | *Marchantia paleacea* subsp. *diptera* |
| 35 | 208544 | b-proteobacteria | Uncultured Burkholderiales bacterium |

TABLE 5

| clone No. | taxonomy ID | blast name | Bacteria |
|---|---|---|---|
| 36 | | Uncultured bacteria | 95% homologous with GenBank: GU117230.1 *Beijerinckia* sp. |
| 37 | | | No insertion into vector |
| 38 | 1282 | firmicutes | *Staphylococcus epidermidis* |
| 39 | | | Plasmid low yield |
| 40 | 1286 | firmicutes | *Staphylococcus simulans* |
| 41 | | | Unsequenceable |
| 42 | 106649 | g-proteobacteria | *Acinetobacter guillouiae* |
| 43 | 330 | g-proteobacteria | *Pseudomonas pseudoalcaligenes* |
| 44 | | | Plasmid low yield |
| 45 | 106649 | g-proteobacteria | *Acinetobacter guillouiae* |
| 46 | 106649 | g-proteobacteria | *Acinetobacter guillouiae* |
| 47 | | | Unsequenceable |
| 48 | | | Plasmid low yield |
| 49 | | | No insertion into vector |
| 50 | 198441 | high GC Gram+ | uncultured *Nocardiodies* sp. |
| 51 | 1747 | high GC Gram+ | *Propionibacterium acnes* |
| 52 | 208544 | p-proteobacteria | uncultured Burkholderales bacterium |
| 53 | | | Unsequenceable |
| 54 | 77133 | Uncultured bacteria | 99% homologous with GenBank: JQ385505.2 Acetobacteraceae |
| 55 | | | Plasmid low yield |
| 56 | 77133 | Uncultured bacteria | 99% homologous with GenBank: HQ905913.1 *Sphingomonas sp* |
| 57 | | | Unsequenceable |
| 58 | 1156809 | a-proteobacteria | Acetobacteraceae bacterium GIMN 1.016 |
| 59 | | | Unsequenceable |

TABLE 5-continued

| clone No. | taxonomy ID | blast name | Bacteria |
|---|---|---|---|
| 60 | 218066 | high GC Gram+ | uncultured *Propionibacterium* sp. |
| 61 | | | Unsequenceable |
| 62 | 338954 | a-proteobacteria | uncultured *Paracraurococcus* sp. |
| 63 | | | Unsequenceable |
| 64 | | | Unsequenceable |
| 65 | 106649 | g-proteobacteria | *Acinetobacter guillouiae* |
| 66 | 1110547 | g-proteobacteria | *Pseudomonas* sp. SD2 (2011) |
| 67 | 93925 | liveworts | *Marchantia paleacea* subsp. *diptera* |
| 68 | | | Unsequenceable |
| 69 | | | Unsequenceable |
| 70 | | | No insertion into vector |

TABLE 6

| clone No. | taxonomy ID | blast name | Bacteria |
|---|---|---|---|
| 71 | 77133 | Uncultured bacteria | 99% homologous with GenBank: DQ532316.1 *Caulobacter* |
| 72 | 77133 | Uncultured bacteria | 99% homologous with GenBank: DQ532316.1 *Caulobacter* |
| 73 | 70131 | mosses | *Climacium dendroides* |
| 74 | | | Unsequenceable |
| 75 | 77133 | Uncultured bacteria | 99% homologous with GenBank: HM366464.1 Acetobacteraceae bacterium |
| 76 | 93925 | liveworts | *Marchantia paleacea* subsp. *diptera* |
| 77 | | | Plasmid low yield |
| 78 | 70131 | mosses | *Climacium dendroides* |
| 79 | 93925 | liveworts | *Marchantia paleacea* subsp. *diptera* |
| 80 | 218066 | high GC Gram+ | uncultured *Propionibacterium* sp. |
| 81 | 77133 | Uncultured bacteria | 98% homologous with GenBank: AM697178.1 *Hymenobacter* |
| 82 | 1054546 | enterobacteria | *Serratia* sp. W2Dec25 |
| 83 | 77133 | Uncultured bacteria | 98% homologous with GenBank: AM697178.1 *Hymenobacter* |
| 84 | 354178 | a-proteobacteria | *Methylobacterium* |
| 85 | | | Unsequenceable |
| 86 | | | Unsequenceable |
| 87 | | | Unsequenceable |
| 88 | | | No insertion into vector |
| 89 | 106649 | g-proteobacteria | *Acinetobacter guillouiae* |
| 90 | | | No insertion into vector |
| 91 | 1282 | firmicutes | *Staphylococcus epidermidis* |
| 92 | | | No insertion into vector |
| 93 | 153809 | proteobacteria | uncultured proteobacterium |
| 94 | | | No insertion into vector |
| 95 | | | No insertion into vector |
| 96 | 106649 | g-proteobacteria | *Acinetobacter guillouiae* |
| 97 | 1156809 | a-proteobacteria | Acetobacteraceae bacterium GIMN 1.016 |
| 98 | 1647640 | g-proteobacteria | *Acinetobacter* sp. AA42 |
| 99 | 218066 | high GC Gram+ | uncultured *Propionibacterium* sp. |
| 100 | | | Unsequenceable |

Figure 8:
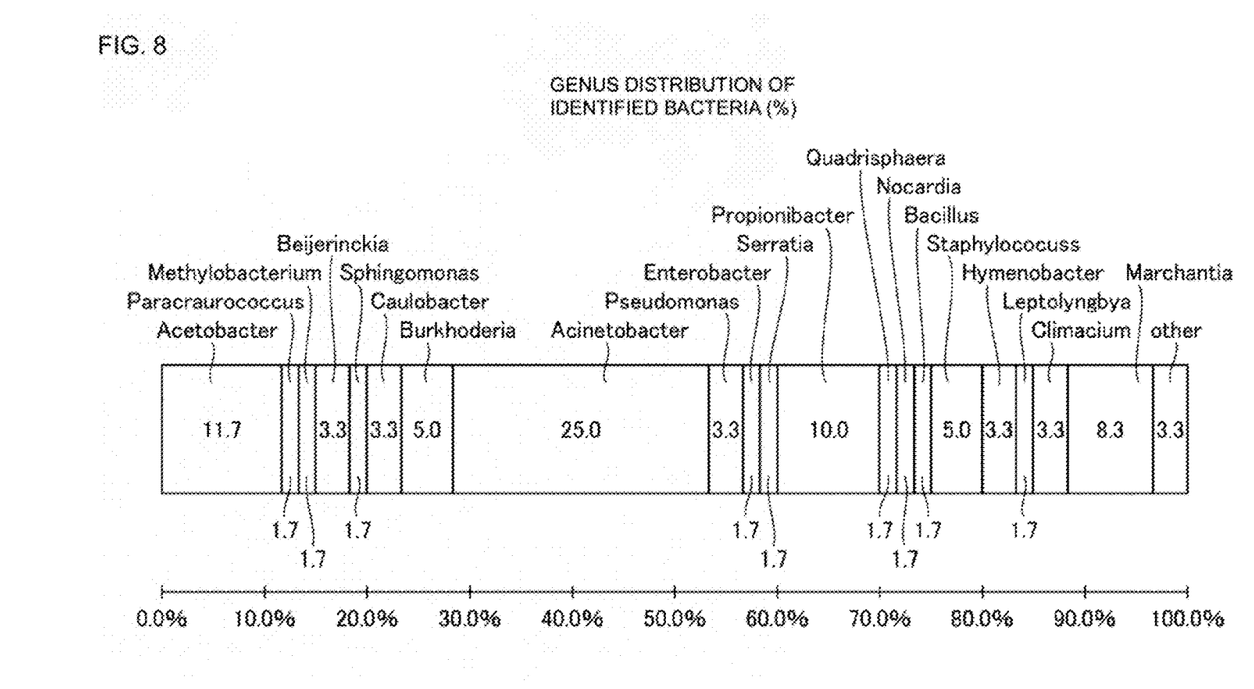
FIG. 8 is a graphical representation of the genus distribution of the bacteria identified in Example 3.

FIG. 8 is a graphical representation of the genus distribution of the above bacteria identified in this example. In FIG. 8, all bacterial species are grouped according to genus. The uncultured bacterium clones in Table 4 are included in the genera with the highest sequence homology (homology: 95% or more) in FIG. 8. The term "not identified bacteria" means that no known genus was found with high homology. The segment "other" means that the most detailed available information is "division" and no information is available on "genus."

The results presented in Tables 4 to 6 and FIG. 8 provide a rough microbial composition of dust in air. In other words, the colony counts of the detected microorganisms (the numbers of duplicates) indicate relative abundances. The detected microorganisms were successfully identified into pathogens (such as Serratia and Nocardia), food spoilage bacteria (such as Enterobacteriaceae), water pollution bacteria (such as Methylobacteria), and so forth. This method can therefore be applied to environmental monitoring at locations where microbial control is necessary, such as hospitals and food factories. Analytical methods based on extraction methods (extraction devices) according to the present invention can also be used to detect microorganisms in a fluid (air).

The embodiments and examples disclosed herein should be construed as being exemplary in all respects rather than being limiting. The scope of the present invention is defined not by the foregoing description but by the claims and is intended to include equivalents to the scope of the claims and all modifications that fall within the scope of the claims.

The present invention is applicable in, for example, the medical and environmental health fields. For example, analysis (e.g., identification and quantification) of bacteria, viruses, and other organisms in air will give analytical results helpful to the prevention of bacterial and viral health hazards.

REFERENCE SIGNS LIST

10, 101, 102, 103 Metal mesh; 12 Syringe barrel; 2 Extraction device; 2a Body; 2b First stacking portion; 2c Second stacking portion; 2d Cover; 20 Pre-filter; 21 Fastener; 22 Air inlet; 23 Air outlet; 24 Aspiration switch; 31 Biological sample; 32 Impurities; 41 Gasket; 42 Plunger; 5 Container; 6 DNA extractant.

The invention claimed is:

1. A method for extracting nucleic acid, the method comprising:
   passing a fluid containing a plurality of intact biological structures, each of which contains nucleic acid and a coating structure covering the nucleic acid, through a metal mesh so as to trap a biological sample containing one or more of the biological structures on the metal mesh;
   immersing the metal mesh, with the biological sample trapped thereon, in a nucleic acid extractant which is a solvent for the nucleic acid but not for the coating structure; and thereafter
   extracting the nucleic acid from the metal mesh and collecting the nucleic acid extractant.

2. The extraction method according to claim 1, wherein the metal mesh has an aperture size which is smaller than the average size of the intact biological structures and larger than the average size of the nucleic acid and, after the extractant separates the nucleic acid from the coating structure of the biological structure, passing the nucleic acid through the metal mesh.

3. The extraction method according to claim 1, wherein the metal mesh is insoluble in the nucleic acid extractant.

4. The extraction method according to claim 1, wherein the nucleic acid extractant contains phenol.

5. The extraction method according to claim 4, wherein the nucleic acid extractant also contains chloroform.

6. The extraction method according to claim 1, wherein trapping the intact biological structures includes removing a material other than the biological structures from the fluid using a pre-filter before trapping the biological sample on the metal mesh.

7. A method for analyzing a biological sample, the method comprising extracting nucleic acid in accordance with claim 1 and thereafter analyzing nucleic acid.

8. A method for extracting nucleic acid from first and second biological samples existing in a fluid, the first biological sample comprising a plurality of intact first biological structures, each of which contains a first nucleic acid and a first coating structure, the second biological sample comprising a plurality of intact second biological structures, each of which contains a second nucleic acid and a second coating structure, the method comprising:
   trapping intact first and second biological structures on first and second metal meshes, respectively, to form first and second biological samples;
   immersing the first and second metal meshes, with the respective first and second biological samples trapped thereon, in a nucleic acid extractant which is a solvent for both the first and second nucleic acids but is not a solvent for the first or second coating structures; and thereafter
   passing the first and second nucleic acids through the first and second metal meshes, respectively, and separately collecting the first and second nucleic acids.

9. A method for extracting nucleic acid in accordance with claim 8, wherein the first metal mesh has an aperture size smaller than the average size of the intact first biological structures and larger than the average size of the first nucleic acid and the second metal mesh has an aperture size smaller than the average size of the intact second biological structures and larger than the average size of the second nucleic acid and, after the extractant separates the first and second nucleic acids from the coating structures of the first and second biological structures, passing the first and second nucleic acids through the first and second metal meshes, respectively.

10. The extraction method according to claim 1, wherein the biological structures are viruses and/or cells.

11. A method for extracting nucleic acid in accordance with claim 8, wherein the biological structures are viruses and/or cells.

* * * * *